US00PP25964P2

(12) United States Plant Patent
Braam

(10) Patent No.: US PP25,964 P2
(45) Date of Patent: Sep. 29, 2015

(54) ***NEPHROLEPIS* PLANT NAMED 'BRAVIT2621'**

(50) Latin Name: *Nephrolepis exaltata*
Varietal Denomination: BRAVIT2621

(71) Applicant: Wim Braam, Kudelstaart (NL)

(72) Inventor: Wim Braam, Kudelstaart (NL)

(73) Assignee: Braam Vitro B.V., De Kwakel (NL)

( * ) Notice: Subject to any disclaimer, the term of this patent is extended or adjusted under 35 U.S.C. 154(b) by 95 days.

(21) Appl. No.: 13/998,706

(22) Filed: Nov. 26, 2013

(51) Int. Cl.
*A01H 5/00* (2006.01)

(52) U.S. Cl.
USPC ..... Plt./379

(58) Field of Classification Search
USPC ..... Plt./379
See application file for complete search history.

*Primary Examiner* — Susan McCormick Ewoldt
(74) *Attorney, Agent, or Firm* — C. A. Whealy

(57) ABSTRACT

A new and distinct cultivar of *Nephrolepis* plant named 'BRAVIT2621' characterized by its compact, upright to outwardly spreading plant habit; dark green-colored pinnae; relative drought tolerance; and good interiorscape performance.

2 Drawing Sheets

Botanical designation: *Nephrolepis exaltata.*
Cultivar denomination: 'BRAVIT2621'.

BACKGROUND OF THE INVENTION

The present invention relates to a new and distinct cultivar of *Nephrolepis* plant, botanically known as *Nephrolepis exaltata,* commonly known as Sword Fern and hereinafter referred to by the name 'BRAVIT2621'.

The new *Nephrolepis* plant is a naturally-occurring whole plant mutation of *Nephrolepis exaltata* 'Emerald Queen', not patented. The new *Nephrolepis* plant was discovered and selected by the Inventor as a single plant within a population of plants of 'Emerald Queen' in a controlled greenhouse environment in De Kwakel, The Netherlands in September, 2011.

Asexual reproduction of the new *Nephrolepis* plant by tissue culture in De Kwakel, The Netherlands, since April, 2012 has shown that the unique features of this new *Nephrolepis* plant are stable and reproduced true to type in successive generations.

SUMMARY OF THE INVENTION

Plants of the new *Nephrolepis* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BRAVIT2621'. These characteristics in combination distinguish 'BRAVIT2621' as a new and distinct *Nephrolepis* plant:

1. Compact, upright to outwardly spreading plant habit.
2. Dark green-colored pinnae.
3. Relatively drought-tolerant.
4. Good interiorscape performance.

Plants of the new *Nephrolepis* differ from plants of the mutation parent, 'Emerald Queen', in the following characteristics:

1. Plants of the new *Nephrolepis* are more compact and are more suitable for smaller containers than plants of 'Emerald Queen'.
2. Plants of the new *Nephrolepis* have shorter fronds than plants of 'Emerald Queen'.
3. Plants of the new *Nephrolepis* are more suitable for interiorscape usage and plants of 'Emerald Queen' are more suitable for outdoor plantings.

Plants of the new *Nephrolepis* can be compared to plants of *Nephrolepis obliterata* 'Kimberly Queen', not patented. Plants of the new *Nephrolepis* differ primarily from plants of 'Kimberly Queen' in the following characteristics:

1. Plants of the new *Nephrolepis* are more compact and are more suitable for smaller containers than plants of 'Kimberly Queen'.
2. Plants of the new *Nephrolepis* have shorter fronds than plants of 'Kimberly Queen'.
3. Plants of the new *Nephrolepis* are more suitable for interiorscape usage and plants of 'Kimberly Queen' are more suitable for outdoor plantings.

BRIEF DESCRIPTION OF THE PHOTOGRAPHS

The accompanying colored photographs illustrate the overall appearance of the new *Nephrolepis* plant showing the colors as true as it is reasonably possible to obtain in colored reproductions of this type. Colors in the photographs may differ slightly from the color values cited in the detailed botanical description which accurately describe the colors of the new *Nephrolepis* plant.

The photograph on the first sheet is a side perspective view of a typical flowering plant of 'BRAVIT2621' grown in a container.

The photograph on the second sheet is a close-up view of the upper and lower surfaces of typical fronds of BRAVIT2621'.

DETAILED BOTANICAL DESCRIPTION

Plants used for the aforementioned photographs and following description were grown during the summer in twoliter containers in a glass-covered greenhouse in De Kwakel, The Netherlands and under cultural practices typical of commercial production conditions. During the production of the plants, day and night temperatures ranged from 18.5° C. to 22.5° C. and light levels averaged 20,000 lux. Plants were one year old when the photographs and description were taken. In the following description, color references are made to The Royal Horticultural Society Colour Chart, 2007 Edition, except where general terms of ordinary dictionary significance are used.

Botanical classification: *Nephrolepis exaltata* 'BRAVIT2621'.

Parentage: Naturally-occurring whole plant mutation of *Nephrolepis exaltata* 'Emerald Queen', not patented.

Propagation:

*Type*.—By tissue culture.

*Time to initiate roots, summer*.—About ten days at temperatures about 21° C.

*Time to initiate roots, winter*.—About two weeks at temperatures about 21° C.

*Time to produce a rooted young plant, summer*.—About five weeks at temperatures about 21° C.

*Time to produce a rooted young plant, winter*.—About six weeks at temperatures about 21° C.

Root description.—Fine, fibrous; white in color.

*Rooting habit*.—Freely branching; dense.

Plant description:

*Plant and growth habit*.—Compact, upright to outwardly spreading plant habit; moderately vigorous to vigorous growth habit; suitable for small containers and interiorscape usage.

*Plant height*.—About 65 cm.

*Plant width*.—About 66 cm.

Frond description:

*Frond length*.—About 41.3 cm.

*Frond width*.—About 5.1 cm.

*Frond shape*.—Narrowly lanceolate.

*Rachis length*.—About 40.9 cm.

*Rachis width*.—About 2 mm.

*Rachis strength*.—Strong, moderately flexible.

*Rachis texture*.—Densely pubescent.

*Rachis/frond orientation*.—Slightly twisted.

*Rachis color*.—Close to N199B; pubescence, close to N167B.

Pinnae description:

*Arrangement*.—Bi-pinnate.

*Quantity per frond*.—About 120.

*Length*.—About 2.8 cm.

*Width*.—About 8 mm.

*Shape*.—Lanceolate; slightly carinate, slightly falcate.

*Apex*.—Acute.

*Base*.—Hastate.

*Margin*.—Serrate.

*Texture, upper and lower surfaces*.—Smooth, glabrous.

*Venation pattern*.—Pinnate.

*Color*.—Developing pinnae, upper surface: Close to 144A. Developing pinnae, lower surface: Between 143C and 144A. Fully developed pinnae, upper surface: Close to N137A; venation, close to 203A. Fully developed pinnae, lower surface: Close to 147B; venation, close to 203A.

*Petioles*.—

*Length* (*proximal pinnae*).—About 6.3 cm.

*Width*.—About 2 mm.

*Texture, upper and lower surfaces*.—Pubescent.

*Color, upper and lower surfaces*.—Close to N199B; proximally, close to 200B.

Spore description: Spore development has not been observed on plants of the new *Nephrolepis*.

Disease & pest resistance: Plants of the new *Nephrolepis* have not been observed to be resistant to pathogens and pests common to *Nephrolepis* plants.

Interiorscape performance: Plants of the new *Nephrolepis* have exhibited good interiorscape performance due to its relative drought tolerance.

Temperature tolerance: Plants of the new *Nephrolepis* have been observed to tolerate high temperatures about 35° C. and to be hardy to USDA Hardiness Zone 10.

It is claimed:

1. A new and distinct *Nephrolepis* plant named 'BRAVIT2621' as illustrated and described.

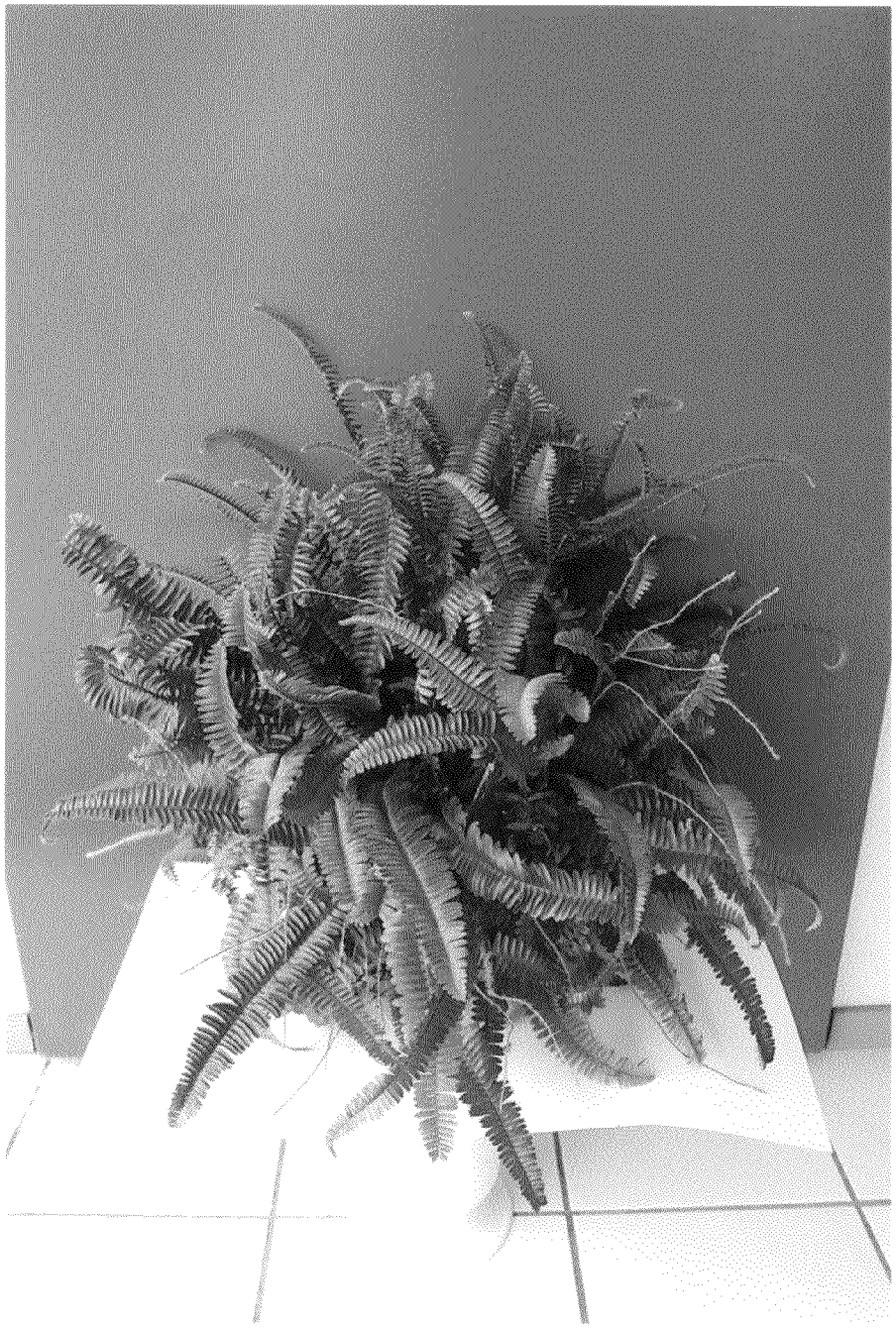

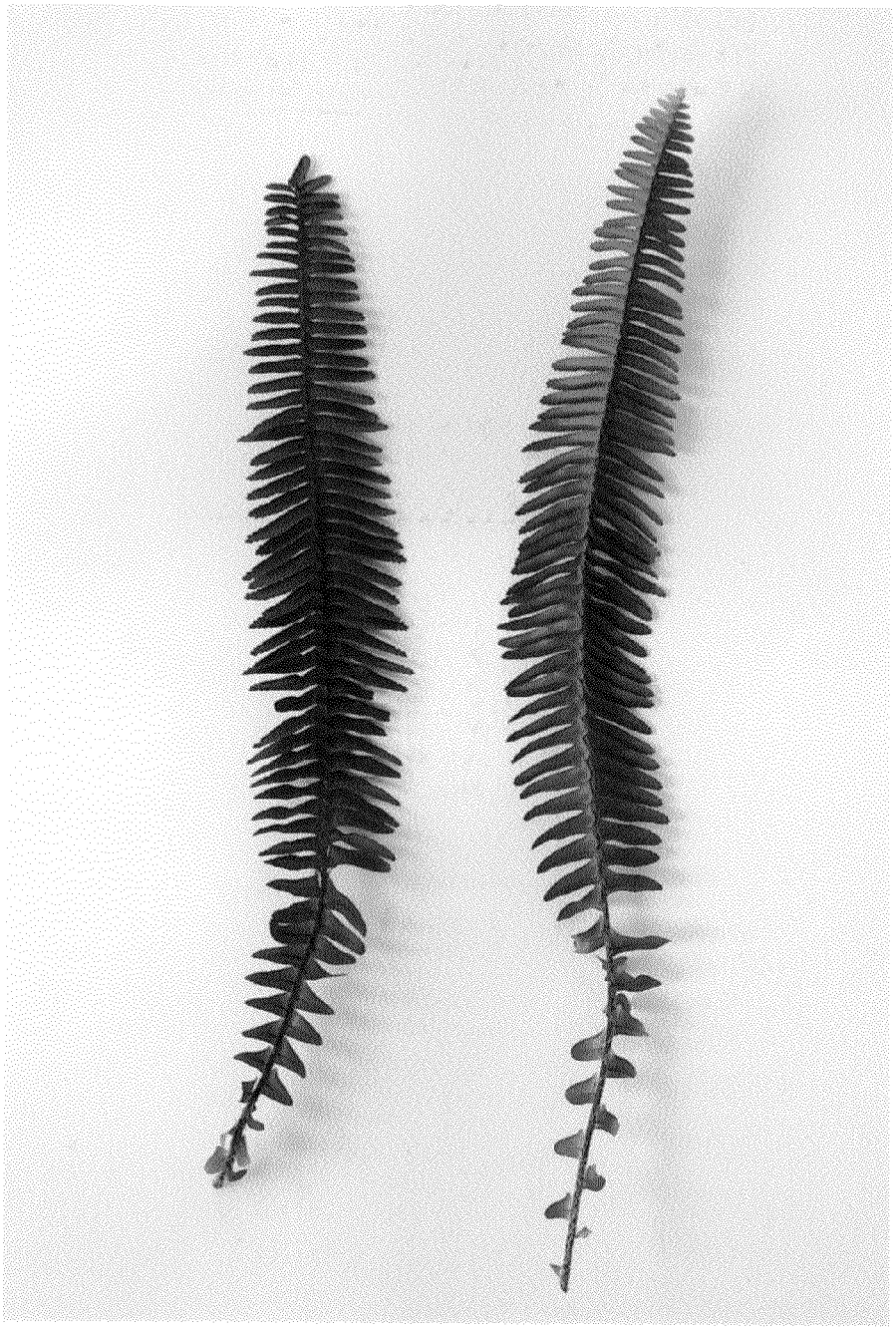

* * * * *